United States Patent [19]

Stauff et al.

[11] 4,017,260

[45] Apr. 12, 1977

[54] METHOD OF MEASURING SULPHUR DIOXIDE

[75] Inventors: Joachim Stauff, Darmstadt; Wolfgang Jaeschke, Kronberg; Gunter Schlögl, Frankfurt, all of Germany

[73] Assignee: Joachim Stauff, Darmstadt, Germany

[22] Filed: July 3, 1974

[21] Appl. No.: 485,324

[30] Foreign Application Priority Data

July 7, 1973 Germany ............... 2334574

[52] U.S. Cl. .................. 23/232 E; 250/362
[51] Int. Cl.² .................. G01N 33/00; G01T 1/20
[58] Field of Search ......... 23/232 R, 232 E, 254 R, 23/254 E, 255 R, 255 E, 230 R; 250/361, 362, 364, 369

[56] References Cited

UNITED STATES PATENTS

| | | | |
|---|---|---|---|
| 3,583,927 | 6/1971 | Schlesinger | 250/483 X |
| 3,659,100 | 4/1972 | Anderson et al. | 23/232 R |
| 3,712,793 | 1/1973 | Lyshkow | 23/232 E |

OTHER PUBLICATIONS

J. Stauff, Chemiluminescence of Some Reactions With Molecular Oxygen, Photochemistry and Photobiology, vol. 4, pp. 1199–1205 (1965).

*Primary Examiner*—Joseph Scovronek
*Attorney, Agent, or Firm*—Ralf H. Siegemund

[57] ABSTRACT

$SO_2$ is extracted from air or other gas mixtures to obtain a water solution, and oxidation is induced in the liquid phase to obtain chemi-luminescence which is photoelectrically detected. The going into solution of $SO_2$ is enhanced by using e.g. $Na_2HgCl_4$. $KMnO_4$, Cerium (IV) sulfate or other oxidizers are used to produce chemiluminescence. The oxidizer is presented in a water solution which may, for example, be atomized into a gas containing $SO_2$.

17 Claims, 2 Drawing Figures

$I_{rel}$ 5 sec.

DETECTOR CURRENT log A

−7

−8

−9

SAMPLE: 5ml SO$_2$ log c (mol/ml)

−10  −9  −8

CONCENTRATION

METHOD OF MEASURING SULPHUR DIOXIDE

BACKGROUND OF THE INVENTION

The present invention relates to a method for determining the content of $SO_2$ and more particularly, the invention relates to a method for causing $SO_2$ to oxidize and for measuring chemi-luminescence as produced during and pursuant to the chemical reaction so as to determine the $SO_2$ content in a gaseous atmosphere, particularly air.

Chemi-luminescence has been observed during reactions involving nitrogen oxide, ozone and other gaseous impurities and pollutants of the air. Accordingly, this phenomenon has been used in rather powerful methods for analytic determination of these pollutants. Usually the test gas is mixed with a reaction medium or reagent, either under normal or under reduced pressure. For example, upon determining the NO content, one will use ozone, or if one wishes to test the ozone content one will use ethylene. As the components so added react the resulting chemi-luminescence is photoelectrically detected; one uses here photomultipliers, secondary electron emission type multipliers etc. The resulting electrical signal is usually amplified and indicated or recorded. The measured value is indicative of the concentration of the substance sought to be detected.

Another known method provides for intimate contact between the test gas and a thin layer of liquid which contains a substance that will react with the substance to be detected under development of luminescence. The U.S. Pat. No. 3,712,793 discloses the detection of $SO_2$ by means of light flashes resulting on contact of that substance with a thin layer of a water solution of ozone.

Another method has become known through one of us, and was published in 1965 in Photochem. Photobiol. Vol. 4, page 1199. In accordance with that method chemi-luminescence is produced in a water solution of $SO_2$, in that sulfite and bisulfite ions thereof react with oxygen in the presence of a catalyst such as iron(III)-hydroxide. Again, the intensity of the luminescence depends on the content of $SO_2$ in the solution. $SO_2$ can be analytically determined in that manner but a gaseous oxidizer such as oxygen itself or ozone will react with a liquid very little or practically not at all, because the concentration of such an oxidizer cannot really be maintained at a sufficiently constant level. On the other hand, if one wants to determine quantitatively a yet unknown substance under utilization of chemi-luminescence, it is imperative to have the substance, with which the unknown substance is supposed to react under development of chemi-luminescence, available at a constant concentration, because the reaction and the resulting phenomenon depends indeed on that concentration.

Utilization of nonspecific oxidizers such as oxygen or ozone has the additional drawback that the test gas (e.g. air) may contain various substances which react also under production of luminescence. For example, ozone when reacting with NO produces chemi-luminescence, even when in the gaseous state, and that luminescence is superimposed upon the one developed and used for detecting the also present $SO_2$.

DESCRIPTION OF THE INVENTION

It is an object of the present invention to determine $SO_2$, particularly when present only at low concentration, even only spuriously, using luminescence produced on oxidation, but avoiding the drawbacks outlined above.

It is a specific object of the invention to detect the $SO_2$ content in gas mixtures or liquids in a rather simple but highly reliable manner.

In accordance with the preferred embodiment of the invention it is suggested to provide for a water phase of the $SO_2$ and cause it to react with a liquid or solid oxidation medium which is likewise contained in a liquidous solvent and at a well defined and established concentration. The intensity of the chemi-luminescence as produced during the reaction is then measured by means of an adequately sensitive light detector. The preferred oxidizers to be employed should have a redox potential in excess of 1.3 volts.

The intensity of the luminescence will be presented and represented in that manner as an electric current or as photon count number per unit time. Either representation is an unambiguous function of the $SO_2$ content in the test solution.

The following materials may serve as specific oxidizers, such as solutions of alkaline bromates, alkaline chlorate, hypoiodites, hypobromites, hypochlorites, chloramine T, peroxidisulfate, cobalt-III-sulfate, potassium permanganate, Cerium (IV) sulfate, sodium periodate or permonosulfuric acid (also called Caro's acid), taken by themselves or mixed with hydrogen peroxide.

Basically, the invention can be practiced with advantage in two ways. In accordance with a first example of the preferred embodiment, $SO_2$ containing gas is passed through water, preferably containing a substance which will bind the $SO_2$. A definite amount of gas (e.g. air) is thereby stripped of its $SO_2$ under utilization of a definite amount of solvent water. That water solution (or a portion thereof) is then mixed with a water solution containing the oxidizer.

In accordance with a second example of the preferred embodiment, the liquid containing the oxidizer is atomized in the gas containing the $SO_2$, and thereby $SO_2$ is extracted from the gas and goes into solution in that liquid.

Combinations of these modes of practicing the invention include for example the atomization of a water solution of a substance that binds $SO_2$, in the gas, followed by exposure to the oxidizer which, however may already be included in that water solution that is being atomized.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

By way of example, 5 milliliters of a solution having $10^{-9}$ mols or 0.064 micrograms $SO_2$ per milliliter, are placed in a suitable, light proof glass container and mixed with 5 ml of a $2 \cdot 10^{-6}$ normal solution of potassium permanganate and 0.01 normal, water sulfuric acid. As soon as the components are mixed a light signal will be produced. A suitably positioned photomultiplier, for example of the variety known under the designation EM1 62 55, indicates that a maximum current of $1 \cdot 10^{-8}$ amperes is produced. This current can be measured with any suitable nano amperemeter or recorder.

Figure 1:
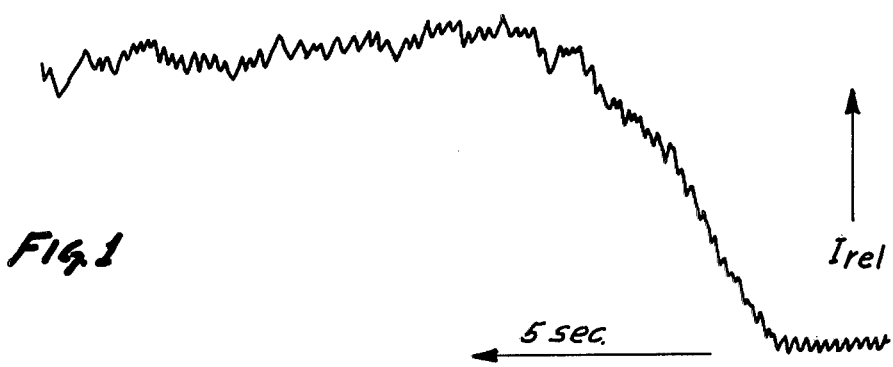
FIG. 1 is a measuring curve which resulted from practicing the invention.

FIG. 1 is a diagram in which photodetector current is plotted against time covering a certain period of reaction and measurement. The method is so sensitive that, on the one hand, maximum (peak value) intensity as measured value, for 5 ml solution, at up to 0.02 microgram test substance can be determined for a signal-to-noise ratio of about 3:1 while, on the other hand integration of the intensity over a period of about 5 seconds yields indication of even below 0.001 micrograms (about $1.5 \cdot 10^{-10}$ mols) test substance. Still higher sensitivity can be obtained when a lock-in amplifier is used with a light chopper being disposed between test container and photomultiplier.

Turning now to more specific applications of the inventive method, the problem exists to measure the $SO_2$ content, for example, in air. A particular, well defined quantity (volume) of the test gas, i.e. air will be run through a solution of $Na_2HgCl_4$ in water. The $SO_2$ is quantitatively removed from the air and goes into water solution. A particular amount, such as 1 to 30 milliliters of that solution will then be placed into a light tight container such as a cuvette, and $KMnO_4$ or Cerium (IV) sulfate solution is added. The resulting chemi-luminescence is registered in a photomultiplier.

Assuming that, for example, one cubic meter air has been passed through 30 ml of a $Na_2HgCl_4$ solution. 15 ml of the resulting solution are then being sampled. It is possible here to detect $2 \cdot 10^{-9}$ mol $SO_2$ per cubic meter air or 0.04 parts per billion. However, the $SO_2$ content in air is normally larger by several orders of magnitude (powers of ten). Thus, one can practice the method by processing a significantly smaller volume of gas in the stated manner.

The high sensitivity of the method permits determination of the $SO_2$ content in gas in that very fine droplets of the liquid containing the oxidizer are dispersed therein. Thus, the liquid offers and exposes a very large surface to the gas (i.e. the sum of the surface of all the droplets) so that the $SO_2$ is very quickly absorbed by the liquid. Accordingly, reaction with the oxidizer occurs immediately, and chemical luminescence is observable accordingly in the cloud of droplets. In effect, one produces a luminous aerosol and the light intensity can be readily detected photoelectrically. Again, the photoelectric current is an unambiguous function of the $SO_2$ content of the gas under examination.

The solution containing the oxidizer can also be distributed (atomized) in a gas stream by means of a spray nozzle, so that the droplets are carried along by the gas flowing at an adjustable velocity. The $SO_2$ content in the gas is immediately picked up by the droplets and oxidized. The gas stream is then run through a container or container portion permitting precipitation of the droplets on a particularly located surface. The light detector is suitably placed to observe the light emanating from that location. Again, the resulting electrical signal indicates luminescence and is proportional to the $SO_2$ content of the gas so tested.

Figure 2:
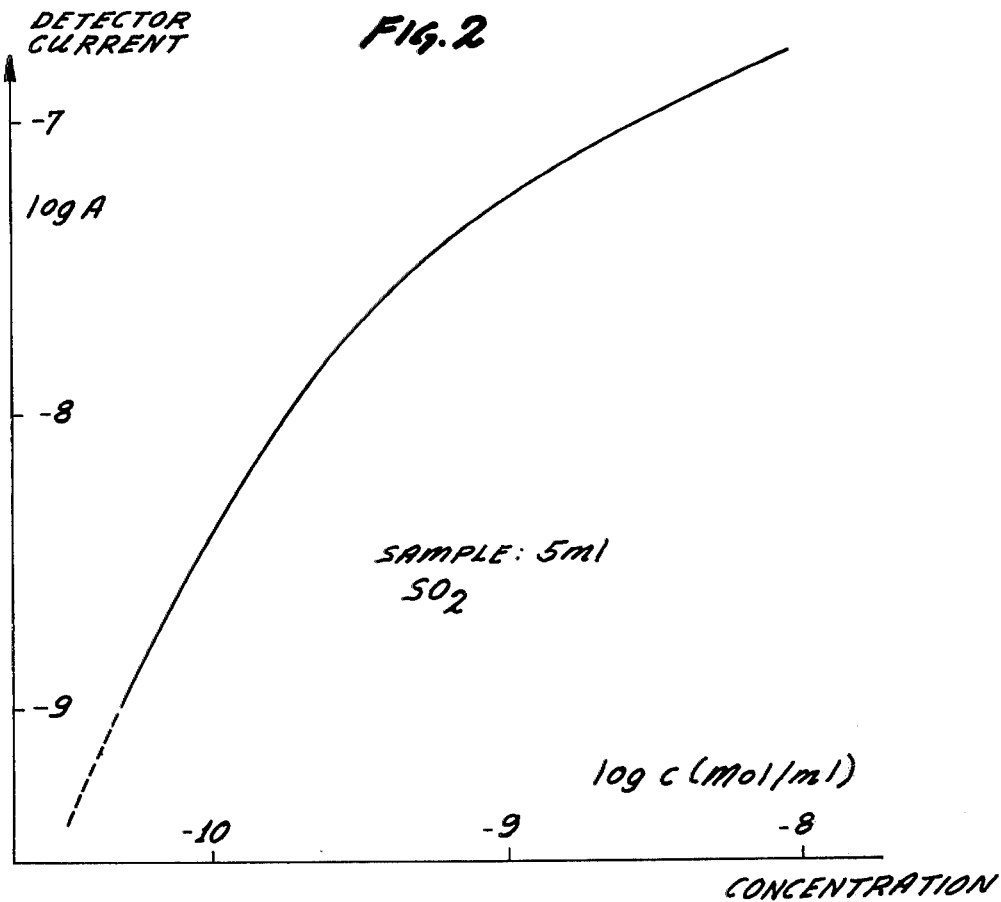
FIG. 2 is a calibration curve to be used for quantitative analysis.

FIG. 2 illustrates a calibration curve (on a log-log scale) relating $SO_2$ content to output current of a particular photodetector. Such a calibration curve is particularly applicable when the composition of the solution or gas under examination is not completely known, and it is merely known or suspected that it does contain $SO_2$, but at an unknown concentration. The curve of FIG. 2 has been arrived at, of course, by relating detection output to known $SO_2$ concentrations.

The inventive method offers, among others, the specific advantage that the presence of NO will not disturb the measurement because the particular oxidizer will not cause NO to undergo chemical luminescence. However $NO_2$ and ozone could be disturbing constituents. NO has an oxidizing effect on $SO_2$ but does not produce luminescence in the process. However, in either case one will stabilize the $SO_2$ by bonding it with $Na_2HgCl_4$. The resulting complex composition will provide for exactly the same chemi-luminescence producing reaction with the (desired) oxidizer as does $SO_2$; the other components will not disturb here.

It was found quite interestingly, that adding of fluorescent substances operates as amplification of significant gain for the chemical luminescence.

The following specific examples demonstrate the invention and its scope more fully.

EXAMPLE 1

10 ml of a solution containing $SO_2$ at $5 \cdot 10^{-8}$ mols per liter was rapidly mixed with 5 ml of a $2 \cdot 10^{-6}$ regular potassium permanganate solution in 0.01 normal sulfuric acid. Mixing occurred inside of a closed, light tight cylindrical glass container by means of suction or spraying. The bottom of this container was placed directly above the light sensitive cathode of a photomultiplier. (Secondary electron multiplier of the EM1 6255A variety). Some aspects of the mixing process is described by one of us and another in Zeitschrift fur physikalishe Chemie Vol. 78 (1972), page 266. The resulting light signal as detected was converted by the multiplier into an electric current of $10^{-8}$ amperes, and amplified in a conventional d.c. amplifier and for example plotted by an oscillograph. The dark current of the multiplier amounted to about $4 \cdot 10^{-10}$ Amp. at room temperature, and a compensating voltage was used to obtain zero output compensation. The compensation current was then used as read-out indicator.

FIG. 1 is actually a characteristic which resulted from practicing the method in accordance with this specific example. The peak value of the curve can be used as representative measured value of the $SO_2$ concentration. Also, the calibration curve of FIG. 2 resulted from practicing this particular example of the inventive method. Solutions of known but different $SO_2$ contents were treated in the stated manner, and the resulting peaks of detected chemi-luminescence were plotted versus the respective $SO_2$ concentration. Thus this curve can now be used upon treating and detecting unknown, test substances in the stated manner and by the same equipment.

EXAMPLE 2

50 liters of air passed through a flow or volume meter and from there through 30 ml of a water solution of 0.1 mol $HgCl_2$ and 0.2 mol $NaCl$ per liter liquid. 10 ml of that solution was mixed with 10 ml of $10^{-4}$ mol of Cerium (IV) sulfate in 0.1 normal sulfuric acid, under utilization of the same equipment outlined in Example 1. A maximum indication of 1.4 microamperes was read from a microampere meter; that value corresponded to a concentration of 0.36 mg $SO_2$ per cubic meter air.

EXAMPLE 3

5 ml of a weak alkaline solution (pH about 11) of $Na_2SO_3$ at a concentration of about $10^{-6}$ (molar) was mixed with 5 ml of a solution containing $10^{-4}$ (molar) of $Na_2SO_4$ and $10^{-2}$ (molar) of $H_2O_2$. The same equipment of Example 1 was used, and chemi-luminescence of 1 to 2 seconds duration was observed producing a photocurrent in the multiplier of $1 \cdot 10^{-7}$ Amp. A modified version of this example was practiced under omission of $H_2O_2$; the resulting light signal was, however, only one third of the previously recorded maximum.

EXAMPLE 4

Bisulfite solution at a concentration of up to $10^{-6}$ (molar) produce chemi-luminescence with either of the oxidizers as used in the preceding examples ($10^{-2}$ molar). If a water $H_2O_2$ solution of eosine with a concentration of $10^{-5}$ was added, the chemi-luminescence was amplified about five-fold, if compared with the signal without the dye. Eosine is a fluorescent substance.

A modification of this example replaces the eosine by quinine sulfate, resulting in a three-fold increase in the peak intensity of measured output. Using riboflavine phosphate results in a four-fold output increase.

EXAMPLE 5

A ball-shaped glass container or balloon containing 2 to 3 liters but having a small flattened window of about 4 cm diameter for planar face-to-face contact or juxtapositioning with the photomultiplier, was provided with a light reflecting layer such as silver or MgO so as to increase the luminous gain. The container had inlet and outlet studs for passing a gas to be examined through the interior of that container. Air was caused to pass through that balloon at a volumetric flow rate of one fourth the container's volume per second.

The container had a cylindrical inlet tube and a spray nozzle was placed therein. A conventional metering pump was used to feed a water solution to the spray nozzle for atomizing the solution so as to produce a fog of tiny droplets to be carried along by the air flow. The liquid contained the oxidizer. The droplet size thus produced depends on the size of the nozzle aperture as well as on the pressure applied to the liquid.

The container or balloon of about 2.3 liters served as reaction vessel to obtain reaction between the $SO_2$ content in the passed air and the oxidizer contained in the droplets. The resulting chemi-luminescence was detected by the photomultiplier and recorded.

In one instance of using this equipment $10^{-5}$ to $10^{-4}$ normal potassium permanganate solution in 0.01 normal sulfuric acid was used as atomized oxidizer. The 2.3 liter balloon as container was used with a throughput of 0.5 liter air per second. The photomultiplier was particularly sensitive to blue luminescence light and produced a steady photocurrent of about 0.5 microamperes. The air flow contained 0.44 mg $SO_2$ per cubic meter as was determined through the chemi-luminescence reaction outline above, in accordance with the description of Example 2.

EXAMPLE 6

15 ml of the $SO_2$ solution as per Example 2 was mixed with 5 ml of a 0.1 molar water solution of $H_2SO_5$ (Caro's acid). The solution had been prepared just prior to usage by diluting concentrated acid. The equipment explained in Example 1 was used here, and the chemi-luminescence resulted in a photocurrent in excess of 2 microamperes.

The invention is not limited to the embodiments described above but all changes and modifications thereof not constituting departures from the spirit and scope of the invention are intended to be included.

We claim:

1. A method for quantitatively detecting $SO_2$ comprising the steps of:
   providing a water solution of the $SO_2$ to be detected;
   exposing the water solution of $SO_2$ to a liquid containing a liquid or a solid oxidizer which oxidizes $SO_2$ to provide chemi-luminescence; and
   photoelectrically detecting the chemi-luminescence and its intensity to obtain a representation of the $SO_2$ concentration in the said water solution.

2. The method of claim 1 wherein the water solution of $SO_2$ and a water solution of the oxidizer are provided separately and the water solutions are mixed using predetermined quantities of each solution to obtain oxidation with chemi-luminescence.

3. The method of claim 1 including extracting the $SO_2$ to be detected from a gas or mixture of gases by causing the $SO_2$ to be absorbed in said water solution of $SO_2$.

4. The method of claim 1 wherein the water solution of the $SO_2$ is produced by contacting an $SO_2$-containing gas with a water solution of the said oxidizer.

5. The method of claim 4 wherein said water solution of oxidizer is atomized into said $SO_2$-containing gas.

6. The method of claim 1 wherein said water solution of $SO_2$ is provided by exposing $SO_2$ to a water solution of a substance which extracts the $SO_2$.

7. The method of claim 6 wherein the water solution which extracts $SO_2$ also contains the said oxidizer.

8. The method of claim 6 wherein the water solution which extracts the $SO_2$ is atomized into a gas containing the $SO_2$.

9. The method of claim 1 wherein said oxidizer is a salt of manganic acid;
   an alkali metal bromate, chlorate, hypoiodite, or hypochlorite;
   a water soluble salt of Cerium or Cobalt;
   a salt of periodic acid; or
   permonosulfuric acid, either alone or mixed with hydrogen peroxide.

10. The method of claim 1 including the additional step of adding a fluorescing substance to the solution prior to the detecting step.

11. The method of claim 1 wherein said oxidizer is potassium permanganate.

12. The method of claim 1 wherein the oxidizer is Cerium (IV) sulfate.

13. The method of claim 1 wherein the oxidizer is Cobalt (III) sulfate.

14. The method of claim 1 wherein the oxidizer is chloramine-T.

15. The method of claim 1 including complexing the $SO_2$ to be detected with a complexing agent that shields the $SO_2$ from reaction with NO, $NO_2$ or ozone while permitting oxidation of $SO_2$ by said oxidizer.

16. The method of claim 15 wherein said complexing agent is $Na_2HgCl_4$.

17. The method of claim 1 wherein said oxidizer has a redox potential in excess of 1.3 volts.

* * * * *